US009320872B2

(12) United States Patent  
Urmey (10) Patent No.: US 9,320,872 B2  
(45) Date of Patent: Apr. 26, 2016

(54) CATHETER POSITIONING SYSTEM (71) Applicant: William F. Urmey, Larchmont, NY (US)

(72) Inventor: William F. Urmey, Larchmont, NY (US)

(*) Notice: Subject to any disclaimer, the term of this patent is extended or adjusted under 35 U.S.C. 154(b) by 0 days.

(21) Appl. No.: 13/649,713

(22) Filed: Oct. 11, 2012

(65) Prior Publication Data

US 2013/0096505 A1  Apr. 18, 2013

Related U.S. Application Data (60) Provisional application No. 61/547,432, filed on Oct. 14, 2011.

(51) Int. Cl.  
*A61M 25/01* (2006.01)  
*A61M 25/06* (2006.01)  
*A61N 1/05* (2006.01)  
*A61N 1/36* (2006.01)

(52) U.S. Cl.  
CPC .......... *A61M 25/013* (2013.01); *A61M 25/0105* (2013.01); *A61M 25/0113* (2013.01); *A61M 25/0606* (2013.01); *A61N 1/0551* (2013.01); *A61N 1/36017* (2013.01); *A61N 1/36021* (2013.01)

(58) Field of Classification Search  
CPC .......... A61M 25/013; A61M 25/0105; A61M 25/0113; A61M 5/1418; A61M 2025/09116; A61M 2025/024; Y10S 24/41; A44B 18/0053; Y10T 24/45215  
USPC ............. 604/164.01, 165.01, 165.02; 24/462, 24/543, 450, 449, 584.1; 251/9, 10; 606/120  
See application file for complete search history.

(56) References Cited

U.S. PATENT DOCUMENTS 4,615,472 A  10/1986  Nash  
4,726,369 A  2/1988  Mar  
4,957,117 A  9/1990  Wysham  
(Continued)

FOREIGN PATENT DOCUMENTS

DE  19826746 C1  11/1999  
EP  1905478 A2  4/2008  
(Continued)

OTHER PUBLICATIONS

International Search Report. PCT/US2012/059911.  
(Continued)

*Primary Examiner* — Theodore Stigell  
*Assistant Examiner* — Benjamin Koo  
(74) *Attorney, Agent, or Firm* — Seth Natter; Natter & Natter (57) ABSTRACT

A catheter positioning system includes a catheter needle assembly comprising a catheter having a permanent hub and a needle carried in the catheter lumen. A releasable clamp is used to compress the catheter against the needle to prevent axial movement of one relative to the other. The clamp is periodically released after being moved a short distance toward the target vessel or nerve and is repositioned a short distance from the skin entry point to further advance the catheter needle assembly. The clamp is configured to be removed from the catheter by movement in a direction other than along the longitudinal axis of the catheter while the catheter hub remains in place. After successful placement of the catheter, the clamp may be snapped apart or opened along a hinge without moving the catheter from its final position.

13 Claims, 4 Drawing Sheets

(56) References Cited

U.S. PATENT DOCUMENTS

| | | | |
|---|---|---|---|
| 5,161,534 | A | 11/1992 | Berthiaume |
| 5,325,746 | A | 7/1994 | Anderson |
| 5,325,868 | A | 7/1994 | Kimmelstiel |
| 5,345,659 | A * | 9/1994 | Allan .................. A43B 11/00 24/442 |
| 5,392,778 | A | 2/1995 | Horzewski |
| 5,423,331 | A | 6/1995 | Wysham |
| 5,505,714 | A | 4/1996 | Dassa et al. |
| 5,630,802 | A | 5/1997 | Moellmann |
| 5,634,475 | A | 6/1997 | Wolvek |
| 5,695,470 | A | 12/1997 | Roussigne |
| 5,871,470 | A | 2/1999 | McWha |
| 6,030,349 | A | 2/2000 | Wilson |
| 6,190,333 | B1 | 2/2001 | Valencia |
| 6,613,014 | B1 * | 9/2003 | Chi ........................ 604/93.01 |
| 6,949,104 | B2 | 9/2005 | Griffis |
| 7,699,809 | B2 | 4/2010 | Urmey |
| 2002/0151850 | A1 | 10/2002 | Ferguson et al. |
| 2004/0059247 | A1 | 3/2004 | Urmey |
| 2004/0162544 | A1 | 8/2004 | Raulerson |
| 2006/0217655 | A1 | 9/2006 | Vitullo et al. |
| 2006/0267063 | A1 | 11/2006 | McDaniel |
| 2008/0082079 | A1 * | 4/2008 | Braga et al. .................. 604/523 |
| 2009/0043287 | A1 * | 2/2009 | Mosler et al. ................. 604/544 |
| 2010/0056910 | A1 | 3/2010 | Yanuma |

FOREIGN PATENT DOCUMENTS

| | | |
|---|---|---|
| EP | 2158932 A2 | 3/2010 |
| WO | WO 2008/076917 A2 | 6/2008 |
| WO | WO 2011/038931 A1 | 4/2011 |

OTHER PUBLICATIONS

Supplementary European Search Report Jan. 15, 2015.

* cited by examiner

CATHETER POSITIONING SYSTEM

RELATED APPLICATIONS

This application claims the benefit of U.S. Provisional Application No. 61/547,432, filed Oct. 14, 2011, the entirety of which is incorporated herein by reference.

BACKGROUND OF THE INVENTION

1. Field of the Invention

This invention relates generally to the placement of intravascular catheters as well as catheters for the administration of regional anesthesia. More particularly, relating to intravascular catheter placement, a system for positioning a catheter for such procedures as central venous pressure monitoring or infusions of fluids or medications. With respect to regional anesthesia, the invention relates to a system for positioning a catheter and nerve stimulator or other needle in conjunction with various procedures, such as, the administration of an anesthetic blockade and for continuous infusion of anesthetic through the catheter.

2. Antecedents of the Invention

The field of regional anesthesia relates to the practice of administering anesthesia to a specific body region during surgery, for the relief of postoperative pain, and for extended relief of trauma or chronic pain. Often, regional anesthesia has been found to be preferable to general anesthesia because of increased safety, the availability of postoperative pain control and decreased anesthetic costs.

Regional anesthesia delivery techniques strove to optimize administration of a local anesthetic in close proximity to a target or nerve plexus so as to establish a neural blockade. Successful administration of regional anesthesia was dependent upon the accurate placement of the anesthetic in relation to the target nerve or nerves.

Various techniques have been employed to assist in placement of an administration needle in close proximity to the target nerve, which was not externally visible. One of the traditional methods of needle placement involved eliciting paresthesia. Among the disadvantages of this technique was the lack of accurate patient responses amongst patients who were disoriented and/or sedated.

A prevalent technique employed the use of nerve stimulators electrically coupled to a nerve stimulator needle. Such method was premised upon the phenomenon that an electrical pulse is capable of stimulating a motor nerve fiber to contract an innervated muscle or cause paraesthesia, in the case of sensory nerve stimulation.

The nerve stimulator needle was placed within the tissue of the patient's body in the vicinity of the nerve to be blocked and then advanced until stimulation of the target nerve was achieved as determined by visually detecting muscle contractions or by eliciting a report that the patient felt the stimulus in response to the current flow through the stimulator needle.

The current supplied by the nerve stimulator was reduced as the nerve stimulator needle was further advanced, until stimulation of the target nerve was achieved using a reduced current level associated with a prescribed distance between the needle tip and the target nerve.

Thereafter, a portion of the anesthetic dose was administered through the needle to terminate the response to the nerve stimulation current. If the response was terminated by the initial administration, the needle was deemed to be properly positioned in proximity to the target nerve and the remaining dose of anesthetic was administered and the needle was withdrawn upon completion of the surgical procedure.

Placement of catheters for continuous infusion of local anesthetics or other drugs during surgical procedures and primarily postoperatively has been achieved by use of an intra-catheter which was placed or threaded through the internal lumen of a larger needle or stiff cannula, or by use of an extra-catheter which was placed or threaded over an internal needle or smaller stiff cannula. Each technique has been associated with certain disadvantages and limitations that have resulted in less than optimal results for achieving successful continuous plexus or nerve block in clinical practice. These disadvantages have severely limited the use of continuous anesthesia or analgesia, resulting in under-utilization of continuous techniques in favor of more predictably successful, less invasive and usually less traumatic and therefore safer nerve or plexus blockade utilizing only a nerve stimulation needle for anesthesia or analgesia administration as previously described.

Problems associated with the use of an intra-catheter included the fact that a very large and therefore more traumatic introducing needle, e.g. 17 or 18, gauge was necessary to allow passage of a smaller usually 19 or 20 gauge flexible catheter. This caused increase pain and discomfort during the placement. The catheter was passed through the bore of the introducing needle with little control of the final position of the distal end of the catheter because the flexibility of the catheter did not allow the practitioner to accurately determine where the catheter will travel once it passed beyond the needle tip.

Stimulating catheters have been developed with a flexible metal stylet inside the catheter which allowed for the ability to electrically stimulate the nerve or nerves, but these too, were difficult to control in terms of the final positioning of the catheter tip once it passed beyond the needle tip.

Another problem with intra-catheter systems has been persistent leaking of the injected medication at the entry point of the removed introducing needle on the skin surface. This occurred because the catheter diameter was smaller than the needle diameter and the diameter of the hole left by the introducing needle. Leakage was especially pronounced after placement of continuous catheters for superficial nerves or nerve plexus.

An additional problem relates to the fact that the catheter passed through a needle does not maintain a predictably straight trajectory once the catheter tip passes beyond the needle tip. This makes visualization of the catheter difficult or impossible when using ultrasonographic imaging to assist in placement of the catheter. A controlled straight trajectory allows precise placement at the proper anatomical position or endpoint when utilizing imaging techniques.

Placement of a catheter through a needle requires the separate attachment of a typically removable hub or mechanism for connecting to larger bore infusion tubing such as intravenous tubing after the external introducing needle is withdrawn over the proximal end of the placed catheter. These affixed hubs have associated disadvantages that include frequent kinking or occlusion of the smaller catheter, disconnection and bacterial or other contamination of the unprotected smaller catheter, or leakage at the connection site.

Major problems associated with the use of an extra-catheter system included the fact that extra-catheters have had to be made of larger gauges than desirable and have been stiffer than desirable to allow adequate stability for advancement over the smaller internal needle. A catheter with the desired flexibility and small diameter was difficult to pass or thread over the needle due to undesired buckling or bending. The length of the extra-catheter was therefore limited because longer extra-catheter systems of very small diameter were too flexible and therefore unstable and difficult to pass. Shorter catheters are not able to reach the more distant desired position required for central venous monitoring or infusions.

The longer a thin catheter or thin needle was, the more unstable it was. This was because each additional unit of length compounded its flexibility. Such catheters would bend when advanced through the skin and deeper tissues, making targeted accurate placement difficult. Additionally, extra-catheters were required to freely slide off of the internal needle, cannula, or stylet and therefore often had undesired movement in relation to the internal needle during use, especially upon advancement and withdrawal. If the extra-catheter was more tightly fitted to the internal needle, withdrawal of the stylet or needle often put undue traction on the catheter, resulting in undesired movement of the catheter tip from the optimal position that was already achieved.

In U.S. Pat. No. 7,699,809, issued to Applicant herein, a system for positioning a catheter that included a nerve stimulator needle carried within the bore of the catheter was described. The needle includes a microelectrode configured as a needle tip protruding beyond the distal end of the catheter. The catheter and needle are fixed against relative axial movement by a releasable clamp which is grasped by the practitioner to compress the catheter bore against the needle without deforming the needle. The clamp is positioned on the catheter at a relatively short distance, e.g. 2 cm, from the skin entry point to minimize flexure when advancing or withdrawing the catheter and needle assembly to simultaneously position the distal end of catheter and needle tip in close proximity to the target nerve or nerve plexus. A plurality of clamps may be employed and each clamp released as it contacts the entry point or a single clamp is released and repositioned after it contacts the entry point.

Upon attaining the desired needle tip position in proximity to the nerve as determined by electrical stimulation, ultrasonographic imaging, etc., a dosage of anesthetic is administered through the needle. With the clamp or clamps fully or partially released so as to fully open the catheter bore, the needle can be freely withdrawn from the catheter. The proximal end of the catheter is thereafter coupled to a syringe, tubing, pump or other device for continuous administration of an anesthetic or other medication.

Presently, 5-6 million central venous catheters (CVC) are placed each year, in the U.S., alone. By contrast to the placement of catheters utilized for regional anesthesia, intravenous catheters require a permanent hub to avoid the serious complication of the accidental placement or migration of the entire catheter into the central or other venous circulation, a so-called "catheter embolization".

Central venous catheter placements have been performed using a technique that was first described by Seldinger in 1953, now referred to as the "Seldinger Technique". The Seldinger methodology has been to access the vein with a large-gauge sharply pointed needle, after which a flexible wire was placed through the lumen of the needle. The needle is then removed over the wire following which, a long flexible central venous catheter with a permanent hub was placed over the wire, often after using a scalpel and firm "dilator" to open a space in the skin and underlying subcutaneous tissue, to facilitate the passage of the softer catheter into the vein. The wire was then removed, leaving the catheter in the desired intravascular final position. Needless to say, the procedure was somewhat traumatic and often led to difficulty and contamination during the process of passing the wire and the exchange between needle, wire, and catheter.

Currently, the advocated methodology for central venous catheter placement involves the use of direct ultrasongraphic imaging to guide the initial needle placement into the targeted vein. After needle placement, the ultrasongraphic probe was put down and the remainder of the procedure done under the older, landmark-based methodology that has been used for more than 50 years. The use of ultrasongraphic guidance has improved success rates and decreased complications when compared to the conventional blind landmark-based technique.

Several major medical societies have now endorsed the use of ultrasongraphic guidance for CVC placement. These include the American Society of Anesthesiologists, the American Society of Echocardiologists, the Society of Cardiovascular Anesthesiologists and the Centers for Disease Control and Prevention.

The risk of complications during conventional central venous catheter placement include pneumothorax (0 to 6.6%), carotid artery puncture (6%), subclavian artery puncture (0.5 to 4%), hemothorax (1%), and unsuccessful placement in the internal jugular vein (12%). Central venous catheter associated infections have been identified as a major cause of hospital morbidity and mortality.

The American Society of Anesthesiologists as well as The American Society of Echocardiography with the Society of Cardiovascular Anesthesiologists have recently published guidelines for CVC placement.

While the use of ultrasongraphic imaging during initial placement has reduced complications and additional imaging during catheter placement will further reduce the risk of complications, there remains a need to simplify CVC placement and further reduce the associated risks.

SUMMARY OF THE INVENTION

A flexible catheter is fitted over a smaller gauge needle, with the needle tip precisely positioned to protrude just beyond the tapered catheter tip. A single-hand releasable, removable, clamp or grip is used to grasp the catheter and needle to prevent axial movement of one relative to the other. The clamp is used to manipulate the needle and catheter assembly as a unit by initially positioning the clamp a short distance, e.g. 2 cm, from the skin entry point to minimize flexure or deformation when introducing and advancing the catheter-needle assembly, preferably under ultrasonographic imaging. The clamp is periodically released after being moved a short distance toward the target vessel or nerve and is repositioned a short distance from the skin entry point to further advance the catheter needle assembly.

In contrast to the previous invention described in U.S. Pat. No. 7,699,809, which is incorporated herein in its entirety by reference, the catheter has a permanent hub or larger lumen connection port at its proximal end for connection to larger bore infusion tubing, e.g. standard intravenous tubing.

An aspect of invention is that the releasable clamp or grip is configured to open or snap apart so that it can be removed from the catheter, with the catheter hub remaining in place. After successful placement of the catheter, the clamp is snapped apart or opened along a hinge without moving the catheter from its final position. This eliminates the need for a subsequently attached connecting hub to couple the small gauge catheter to standard intravenous or other larger gauge tubing and significantly, enables CVC placement.

From the foregoing compendium, it will be appreciated that a feature of the present invention is to provide a catheter positioning system of the general character described which simplifies CVC placement procedures.

A consideration of the present invention is to provide a catheter positioning system of the general character described which increases the efficiency of intravascular catheter placement.

An aspect of the present invention is to provide a catheter positioning system of the general character described suitable for implementation with catheters having permanent hubs.

A further consideration of the present invention is to provide a catheter positioning system of the general character described which avoids the necessity of making incisions during CVC placement.

To provide a catheter positioning system of the general character described which is well suited for continuous regional anesthesia or analgesia is a further consideration of the present invention.

Yet another aspect of the present invention is to provide a catheter positioning system of the general character described which facilitates simple and accurate positioning of a catheter.

A still further feature of the present invention is to provide a catheter positioning system of the general character described which is relatively low in cost.

An additional consideration of the present invention is to provide a catheter positioning system of the general character described with reduced patient trauma.

A further aspect of the present invention is to provide a catheter positioning system of the general character described with reduced risk of complications.

Another consideration of the present invention is to provide a catheter positioning system for CVC placement of the general character described which eliminates the need for a separate wire guide.

Other aspects, features and considerations of the present invention in part will be obvious and in part will be pointed out hereinafter.

With these ends in view, the invention finds embodiment in certain combinations of elements, arrangements of parts and series of steps by which the aforesaid aspects, features and considerations and certain other aspects, features and considerations are attained, all with reference to the accompanying drawings and the scope of which will be more particularly pointed out and indicated in the appended claims.

DESCRIPTION OF THE DRAWINGS

In the accompanying drawings in which is shown some of the various possible exemplary embodiments of the invention.

DESCRIPTION OF THE INVENTION

Referring now in detail to the drawings, wherein like numerals designate like components throughout, the reference numeral 10 denotes generally a catheter positioning system constructed in accordance with and embodying the invention. The catheter positioning system 10 includes a catheter needle assembly 12 comprising a thin, e.g. 27 gauge, needle 14 having a sharp cutting tip 16 at a distal end.

A thin, e.g. 22 gauge, catheter 18 includes a tapered distal end 20, a permanent hub 22 at its proximal end and a lumen 24 which receives the shaft of the needle 14. The diameter of the lumen 24 is greater than the diameter of the needle shaft, leaving a clearance space 26 such that if unrestrained, the needle 14 may move axially relative to the catheter 18 with relative freedom.

Figure 1:
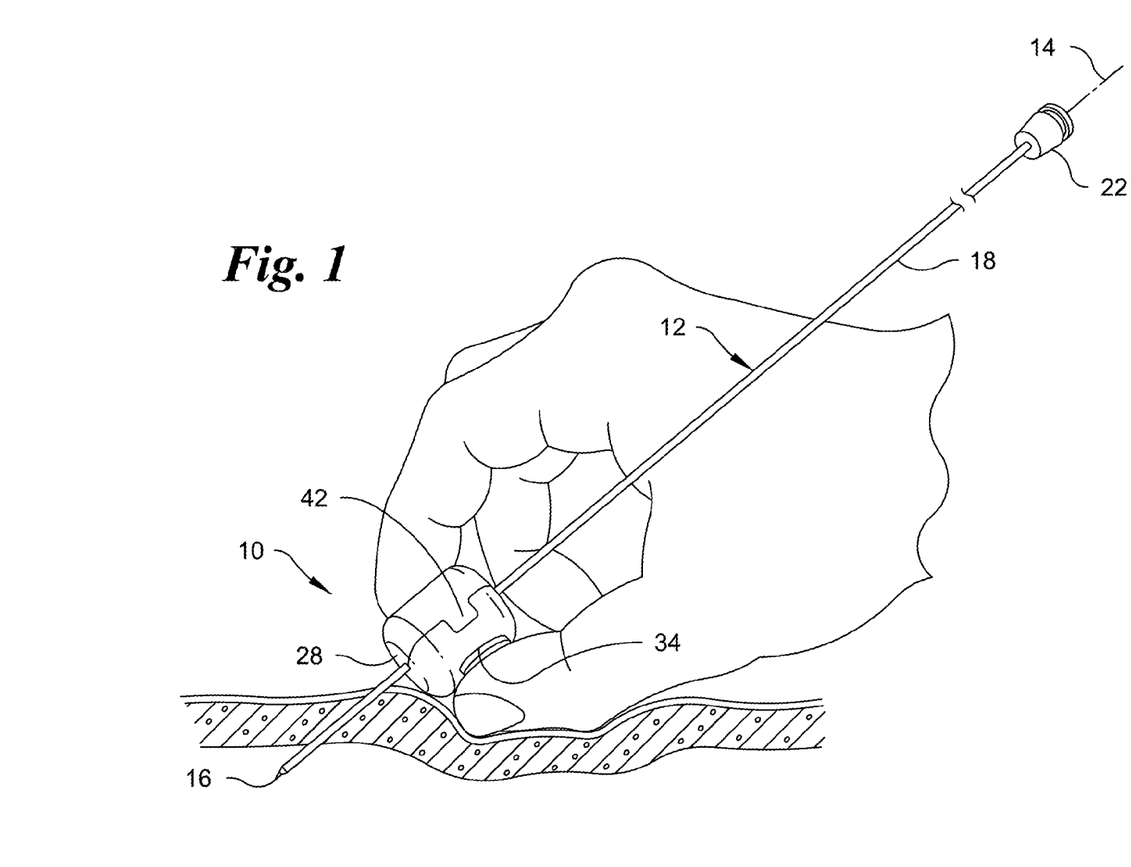
FIG. 1 is an elevational view of a practitioner advancing a catheter and needle assembly by grasping a clamp in accordance with the invention.

Pursuant to the invention, there is provided one or more releasable clamps 28 through which the catheter needle assembly 12 extends. Illustrated in FIG. 1 is an exemplary releasable clamp 28 having a bore 30 through which the catheter needle assembly 12 is threaded and a pair of diametrically opposed cylindrical gates 32 which extend along an axis perpendicular to the axis of the bore 30. Each gate 32 includes an enlarged head 34. Positioned within annular channels registered with the heads 34 are a pair of coil springs 36 which urge the gates 32 radially outwardly to a released position, wherein the clearance space 30 is maintained. By pressing both heads 34 inwardly, the gates deform the catheter 18 to axially fix the catheter 18 relative to the needle shaft, as illustrated in FIG. 2.

Figure 2:
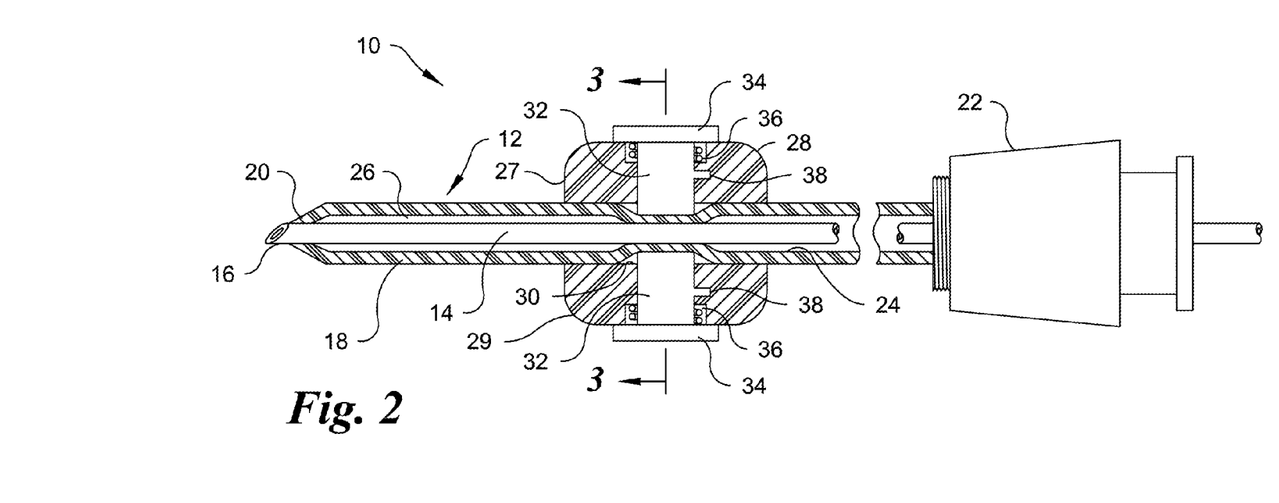
FIG. 2 is an enlarged scale axial sectional view through the catheter and needle assembly and illustrating a permanent hub affixed to the end of the catheter.
Figure 3:
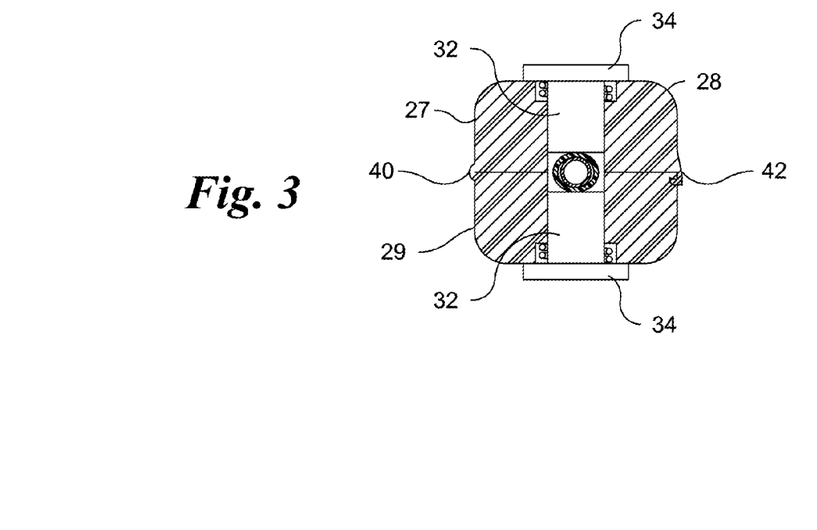
FIG. 3 is a transverse sectional view through the clamp, taken along the plane 3-3 of FIG. 2 showing a living hinge and a flexible latch for opening the clamp.

As will be noted from an examination of FIG. 2 and FIG. 3, when the enlarged heads 34 are pressed inwardly, they engage the outer surfaces of the clamp 28 surrounding the annular coil spring channels and thus provide limit stops, limiting further inward movement of the gates and preventing the gates 32 from deforming the shaft of the needle 14.

The compressed state of the gates can be locked by rotating the heads 34, such that a radially projecting pin 38, normally seated in an axial groove, extends into an annular notch or groove. The gates are released by rotating the heads 34 in the opposite direction to reseat the pins in their axial grooves.

A clamp 28 having a single gate 32 may also be employed, with the catheter being compressed between the single gate and the diametrically opposed portion of the bore 30 to fix the conduit relative to the needle shaft.

The clamp 28 differs, however, from the clamp described U.S. Pat. No. 7,699,809 so as to enable the clamp 28 to be removed from the catheter 18. Because the proximal end of the catheter has affixed thereto the hub 22, the clamp 28 can no longer be removed by sliding off the proximal end of the catheter.

With reference to FIGS. 1-3, it will be seen that the clamp 28 comprises two segments 27, 29, with one half of the bore 30 (split along an axial plane) being formed in each segment. The segments 27, 29 pivot about a living hinge 40 after a flexible latch 42 is released to thereby open the bore 30 of the clamp for removal of the clamp 28 from the catheter 18.

Figures 4, 5:
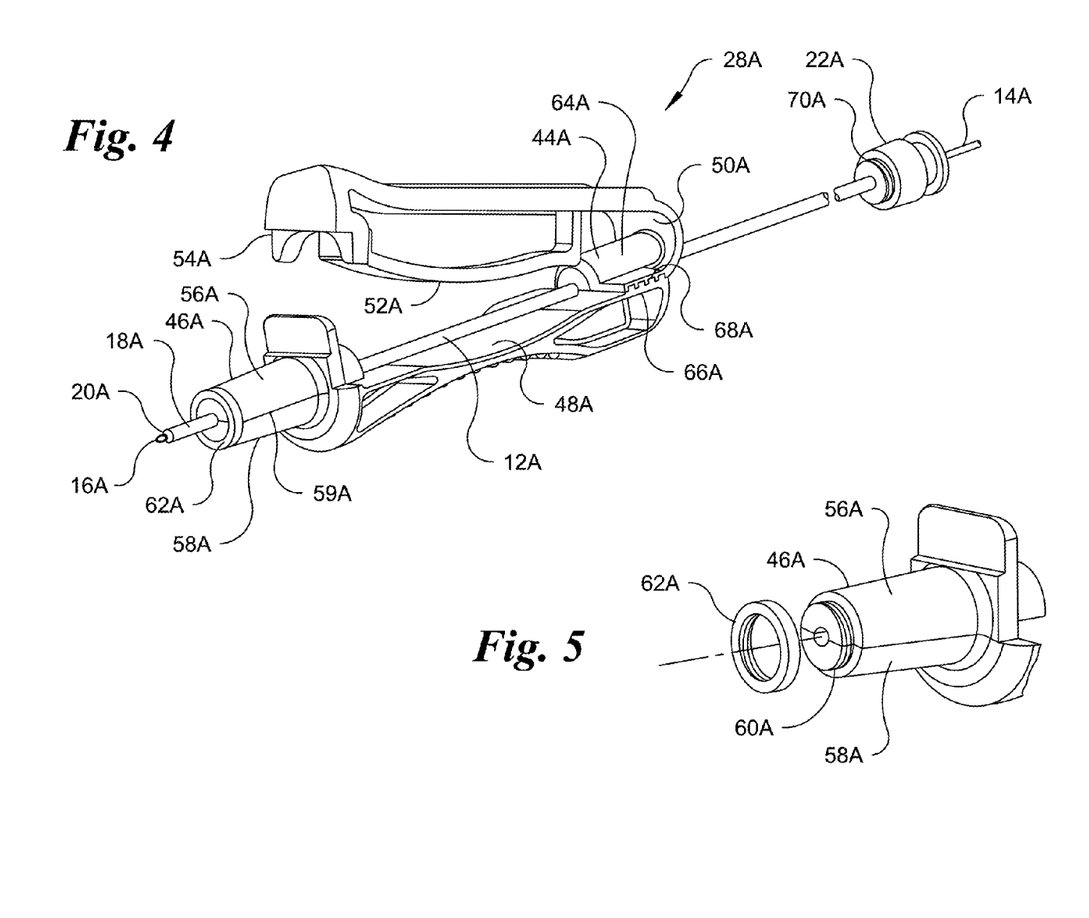
FIG. 4 is an isometric view of a catheter and needle assembly with an alternate snap apart clamp and showing a distal guideway secured by a threaded collar and a proximal guideway, both configured to snap apart for removal of the catheter.
FIG. 5 is an enlarged scale fragmentary exploded isometric view of the distal guideway with the collar removed.

Illustrated in FIG. 4 is an alternate clamp 28A, similar to that described in U.S. Pat. No. 7,699,809. The clamp 28A is formed of molded thermoplastic construction and includes a pair of axially registered generally cylindrical proximal and distal guideways 44A, 46A through which a catheter needle assembly 12A extends. It should be noted that the portion of the catheter needle assembly projecting from the distal guideway 46A includes a needle tip 16A and a distal end taper 20A of a catheter 18A.

The releasable clamp 28A includes a concave platen 48A which extends between the guideways 44A, 46A. A flexible leaf hinge 50A joins the proximal guideway 44A to a maxillary convex jaw 52A. A yoke 54A, at the distal end of the convex jaw 52A, contacts the guideway 46A to provide a limit stop, limiting the travel of the convex jaw 52A and preventing permanent deformation of the nerve stimulator needle 14A. In use, a practitioner grasps the outer surfaces of the convex jaw and the concave platen between the forefinger and thumb and squeezes the jaw and platen together.

It should be appreciated that when the convex jaw is urged against the concave platen, the convex jaw contacts the catheter and deforms it toward the concave platen such that the catheter and the needle are fixed against axial movement relative to one another. The arc of curvature of the mating convex jaw and concave platen may be such to slightly bend, but not permanently deform the nerve stimulator needle.

In order to facilitate removal of the alternate clamp 28A from the catheter assembly 12A, the distal guideway 46A is formed of a pair of break away segments 56A, 58A, joined along a substantially horizontal (as viewed in FIG. 4) axial plane 59A which extends through a bore of the guideway 46A which receives the catheter needle assembly. One half of the bore is formed in each segment 56A, 58A.

A most distal portion of the distal guideway 46A includes a threaded nipple 60A. An annular member, such as an internally threaded collar 62A, circumscribes a portion of the clamp, such as the threaded nipple 60A when the clamp 28A is being used. When the catheter needle assembly has reached its final position and the clamp 28A is to be removed, the threaded collar 62A is disengaged from the nipple 60A and the segments 56A, 58A are separated.

Similarly, the proximal guideway 44A is formed of a pair of upper and lower segments 64A, 66A with one half of a bore carrying the catheter needle assembly being formed in each segment. The segments 64A, 66A, are joined along a corrugated, generally horizontal seam 68A to be snapped apart for removal of the clamp 28A from the catheter needle assembly. The hinge 50A and maxillary convex jaw 52A are preferably formed in one piece with the upper segment 64A.

After removal of the clamp 28A, the threaded collar 62A may be secured to the hub 22A, which includes a threaded nipple 70A for receiving the collar.

A description of usage of the present invention in connection with nerve anesthesia or analgesia via catheter infusion as well as central venus or other intravascular placement of a flexible catheter follows:

Peripheral or Plexus Nerve Anesthesia/Analgesia Via Catheter Infusion:

The flexible catheter, e.g. 20 gauge, is fitted over a smaller gauge needle, e.g. 24 gauge, either stimulating or non-stimulating needle, with the needle tip precisely fitted to protrude just beyond the tapered catheter tip. A single-hand releasable, removable, clamp or grip is used to grasp the catheter and needle to prevent axial movement of one relative to the other. This is used to introduce the needle and catheter as in U.S. Pat. No. 7,699,809 by initially positioning the clamp a short distance, e.g. 2 cm, from the skin entry point to minimize flexure or deformation when introducing the catheter-needle system. The clamp is periodically released after being moved more proximal a short distance to further advance the catheter and needle. In contrast to U.S. Pat. No. 7,699,809, the catheter has a permanent hub or larger lumen connection port for connection to larger bore infusion tubing, e.g. standard intravenous tubing.

An aspect of the present invention is that the adjustable clamp contains a "break-away" hinge allowing the clamp to be removed with only the permanently hubbed catheter remaining in place. This eliminates the need for a subsequently attached connecting hub to couple the small gauge catheter to standard intravenous or other larger gauge tubing. After successful placement, the clamp is broken away to leave the catheter in the final position.

Figure 6:
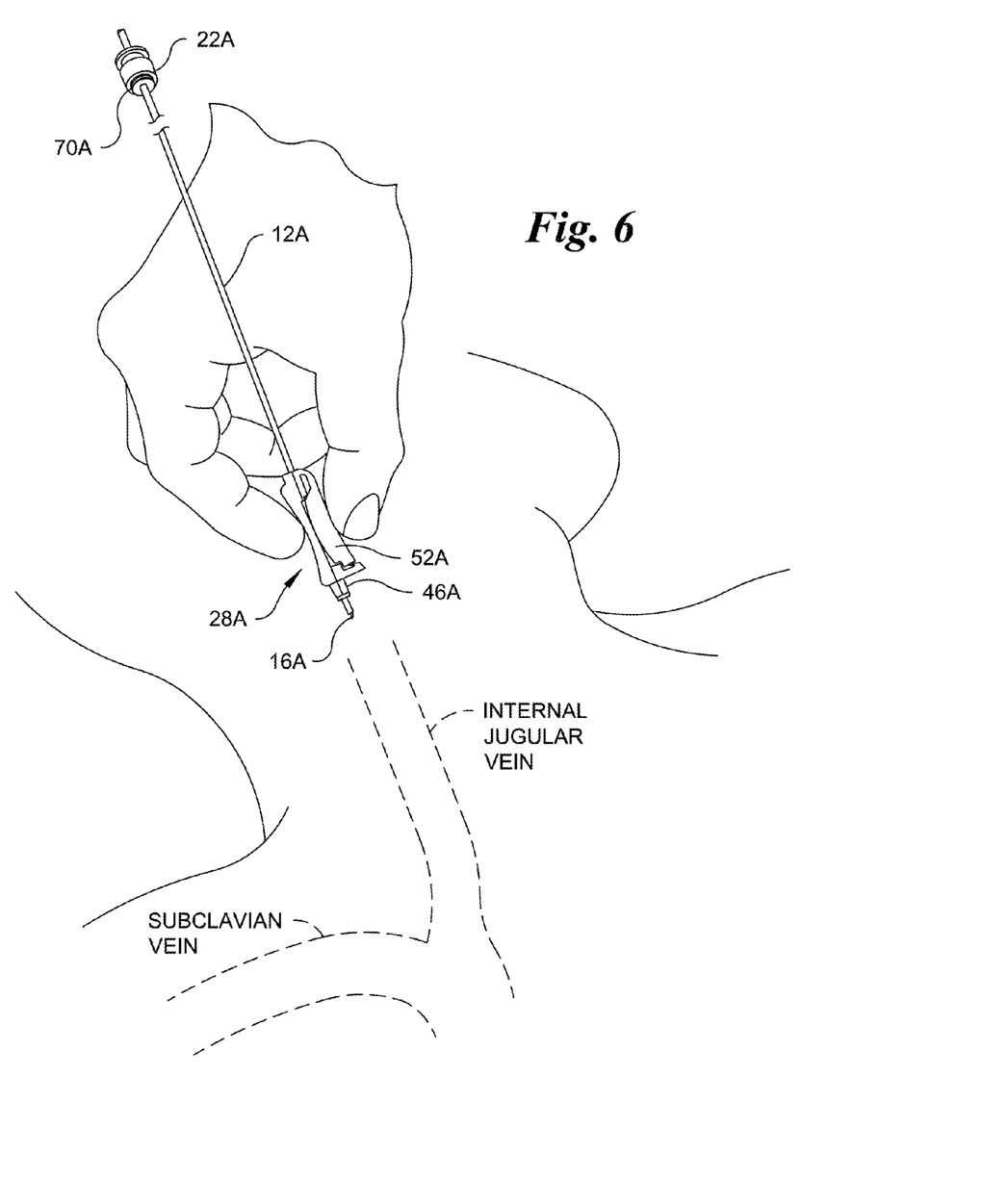
FIG. 6 is a diagrammatic illustration of the catheter and needle assembly and the alternate clamp during an intravascular placement procedure.

Central Venous or Other Intravascular Placement of a Small Gauge Flexible Catheter:

Although the system can be used to place a catheter intravascularly without ultrasonographic imaging modalities, the preferred technique or method involves the use of ultrasonographic imaging to ascertain the correct placement of the needle and catheter tip in the proper vessel, e.g internal jugular vein. This is confirmed by aspiration through the hub of the inner needle. The flexible catheter for central line placement is typically larger, e.g. 16 gauge, than the perineural catheter described above. The releasable clamp 28, 28A is used in a similar method as described above for perineural catheter placement. The catheter is compressed against the smaller internal needle, e.g. 18 gauge, and inserted with the aid of ultrasonographic imaging until the needle and catheter tip are well within the desired vessel, e.g. proximal internal jugular vein, in the neck.

This is confirmed by aspiration of venous blood from the needle hub. The clamp or grip is then released, allowing free axial movement of the needle relative to the overlying catheter. The needle is withdrawn a small distance, e.g. 4 mm, so that the sharp needle tip is fully within the lumen of the catheter and the vessel is therefore protected from damage from the needle tip. The clamp is used to re-grip the catheter needle assembly approximately 2 cm from the skin entry point and is used to advance the needle and catheter into the more distal jugular vein a short distance, e.g. 1 cm. In the preferred method, the needle is then completely removed from within the lumen of the catheter and the clamp is used to grip and advance the central venous catheter in approximately 2 cm increments to the desired endpoint.

An alternative method entails removal of the needle at the same point described above and substitution of the needle with a precisely fitted internal flexible wire such as a J-wire which is then either placed through the catheter and the catheter subsequently passed over, or alternatively placed within the catheter for added stability forming a catheter wire assembly and the releasable clamp or grip used to advance the two together in approximately 2 cm increments while maintaining the relative axial position of each with regard to the other.

Following achievement of the endpoint with any of the above methods, once the catheter is in the desired final position, the clamp or grip is "broken-away" and the catheter affixed to the skin using standard methodology for central venous catheters. This eliminates a step in the present prevailing method for central line catheterization that is associated with instability of the needle relative to the vessel during standard central venous line placement and therefore simplifies central venous catheter placement.

Thus it will be seen that there is provided a catheter positioning system which achieves the various aspects, features and considerations of the present invention and which is well suited to meet the conditions of practical usage.

As various possible further embodiments might be made of the present invention and various changes might be made in the illustrative embodiments above set forth without departing from the spirit of the invention, it is to be understood that all matter herein described or shown in the accompanying drawings is to be interpreted as illustrative and not in a limited sense.

Having thus described the invention, there is claimed as new and desired to be secured by Letters Patent:

1. A system for positioning a flexible catheter, the system comprising a catheter needle assembly, the assembly including a catheter having a distal end, a proximal end having a hub permanently affixed thereto and a lumen, a needle, the needle including a shaft positioned within the lumen, the shaft having a diameter less than that of the lumen leaving a clearance space, the needle having a sharp tip, a distal portion of the needle projecting beyond the distal end of the catheter, the system further including a clamp positioned over the catheter and the needle shaft, the clamp releasably compressing the catheter lumen against the needle shaft to fix the catheter and needle shaft against axial displacement relative to one another, the clamp being manipulated to position the catheter, the clamp comprising one pair of separable segments, the segments being separated to remove the clamp from the catheter after the distal end of the catheter is at a desired position, the clamp further including an annular collar circumscribing at least a portion of the clamp, the annular collar being coaxial with the catheter lumen, the annular collar being disengaged for separation of the one pair of segments and removal of the clamp from the catheter.

2. A system for positioning a flexible catheter as constructed in accordance with claim 1 wherein the clamp includes an other pair of segments.

3. A system for positioning a flexible catheter as constructed in accordance with claim 2 wherein the other pair of segments is adapted to snap apart for separation and removal of the clamp from the catheter.

4. A system for intravascular placement of positioning a flexible catheter as constructed in accordance with claim 2 wherein the other pair of segments form a proximal guideway and the one pair of segments form a distal guideway, portions of the catheter needle assembly extending through each guideway, beyond the distal guideway and between the guideways.

5. A system for positioning a flexible catheter as constructed in accordance with claim 4 wherein a platen extends between a lower segment of the proximal guideway and a lower segment of the distal guideway and a jaw extends from an upper segment of the proximal guideway toward the distal guideway, the catheter needle assembly being positioned between the platen and the jaw.

6. A system for intravascular placement of positioning a flexible catheter as constructed in accordance with claim 1 wherein the segments form a guideway and a portion of the catheter needle assembly extends through the guideway.

7. A system for positioning a flexible catheter as constructed in accordance with claim 1 wherein the clamp includes a bore, the catheter and needle shaft being positioned within the bore the bore having an axis coaxial with the annular collar circumscribing at least a portion of the clamp.

8. A system for positioning a flexible catheter as constructed in accordance with claim 1 wherein the portion of the clamp comprises a nipple engaged by the annular collar, the annular collar being disengaged from the nipple for separation of the segments.

9. A system for positioning a flexible catheter, the system comprising a catheter needle assembly, the catheter needle assembly including a catheter having a distal end, a proximal end having a hub and a lumen, a needle, the needle including a shaft positioned within the lumen, a distal portion of the needle projecting beyond the distal end of the catheter, the system further including a clamp positioned over the catheter and the needle shaft, the clamp releasably compressing the catheter lumen against the needle shaft to fix the catheter and needle shaft against axial displacement relative to one another, the clamp being manipulated to advance the sharp tip and distal end of the catheter toward a target nerve or vessel, wherein the hub is permanently affixed to the catheter at the proximal end and the clamp comprises separable segments, the segments being separated to remove the clamp from the catheter without disturbing the permanently affixed catheter hub after the distal end of the catheter is at a desired position, the system further including a threaded collar for restraining the segments against separation, the threaded collar being in threaded engagement with mating threads formed on the clamp, the threaded collar being disengaged from the mating threads formed on the clamp for separation of the segments.

10. The improved system for positioning a flexible catheter as constructed in accordance with claim 9 wherein the clamp includes a nipple, the mating threads being formed in the nipple.

11. The improved system for positioning a flexible catheter as constructed in accordance with claim 9 wherein the clamp includes an other pair of segments.

12. The improved system for positioning a flexible catheter as constructed in accordance with claim 11 wherein the other pair of segments forms a proximal guideway and the one pair of segments forms a distal guideway, a bore extending through each guideway, portions of the catheter needle assembly extending through the bore of each guideway, beyond the distal guideway and between the guideways.

13. The improved system for positioning a flexible catheter as constructed in accordance with claim 9 wherein the clamp includes a bore having an axis, the catheter being positioned in the bore and the segments are adapted for separation along an axial plane of the bore.

* * * * *